(12) United States Patent
Lauf et al.

(10) Patent No.: US 12,364,610 B2
(45) Date of Patent: Jul. 22, 2025

(54) EXPANDABLE IMPLANT WITH PIVOTING CONTROL ASSEMBLY

(71) Applicant: Life Spine, Inc., Huntley, IL (US)

(72) Inventors: Garrett Lauf, Hampshire, IL (US); Brett Nowak, Lake in the Hills, IL (US); Daniel Predick, Wheat Ridge, CO (US); Paul Christopher Zakelj, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 42 days.

(21) Appl. No.: 17/990,101

(22) Filed: Nov. 18, 2022

(65) Prior Publication Data

US 2023/0079129 A1 Mar. 16, 2023

Related U.S. Application Data

(63) Continuation of application No. 17/014,546, filed on Sep. 8, 2020, now Pat. No. 11,554,020.

(51) Int. Cl.
*A61F 2/44* (2006.01)
*A61F 2/30* (2006.01)

(52) U.S. Cl.
CPC .......... *A61F 2/442* (2013.01); *A61F 2/30744* (2013.01); *A61F 2002/30224* (2013.01);
(Continued)

(58) Field of Classification Search
CPC .... A61F 2/44; A61F 2002/443; A61F 2/4455; A61F 2/442; A61F 2/4425
See application file for complete search history.

(56) References Cited

U.S. PATENT DOCUMENTS

| 904,434 A | 11/1908 | Huff |
| 1,925,385 A | 9/1933 | Humes |

(Continued)

FOREIGN PATENT DOCUMENTS

| CN | 102427769 A | 4/2012 |
| CN | 205866898 U | 1/2017 |

(Continued)

OTHER PUBLICATIONS

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.

(Continued)

*Primary Examiner* — Matthew J Lawson
(74) *Attorney, Agent, or Firm* — Foley & Lardner LLP

(57) ABSTRACT

An expandable implant includes a lower support; an upper support pivotally coupled to the lower support and including a control channel; and a control assembly. The control assembly includes a control shaft coupled to the lower support and a control member coupled to the control shaft and configured to move along the control shaft. The control member includes a base member and a pivot member pivotally coupled to the base member, the pivot member configured to move within the control channel. Movement of the control member along the control shaft causes the pivot member to pivot relative to the base member, and the upper support to pivot relative to the lower support.

19 Claims, 7 Drawing Sheets

(52) U.S. Cl.
CPC .............. *A61F 2002/30405* (2013.01); *A61F 2002/30528* (2013.01); *A61F 2002/30538* (2013.01)

(56) References Cited

U.S. PATENT DOCUMENTS

| | | | |
|---|---|---|---|
| 3,846,846 A | 11/1974 | Fischer |
| 4,466,426 A | 8/1984 | Blackman |
| 4,636,217 A | 1/1987 | Ogilvie et al. |
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,723,126 B1 | 4/2004 | Berry |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,854,766 B2 | 12/2010 | Moskowitz et al. |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 | 1/2012 | Olmos et al. |
| 8,187,332 B2 | 5/2012 | McLuen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | McLuen et al. |
| 8,628,578 B2 | 1/2014 | Miller et al. |
| 8,632,595 B2 | 1/2014 | Weiman |
| 8,641,764 B2 | 2/2014 | Gately |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |

(56) References Cited

U.S. PATENT DOCUMENTS

| | | |
|---|---|---|
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | McLuen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,238,503 B2 * | 3/2019 | Branch ................. A61F 2/4465 |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,363,142 B2 | 7/2019 | McClintock et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,441,430 B2 * | 10/2019 | Ludwig ................. A61F 2/442 |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |

(56) References Cited

U.S. PATENT DOCUMENTS

| | | |
|---|---|---|
| 10,709,575 B2 | 7/2020 | Robinson |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,888,431 B1 | 1/2021 | Robinson |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,051,951 B2 | 7/2021 | Robinson et al. |
| 11,065,128 B2 | 7/2021 | Zappacosta et al. |
| 2002/0010472 A1 | 1/2002 | Kuslich et al. |
| 2002/0029084 A1 | 3/2002 | Paul et al. |
| 2002/0128716 A1 | 9/2002 | Cohen et al. |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0312837 A1 | 12/2009 | Eisermann et al. |
| 2010/0082109 A1 | 4/2010 | Greenhalgh et al. |
| 2010/0179655 A1 | 7/2010 | Hansell et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0029636 A1 | 2/2012 | Ragab et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0221051 A1 | 8/2012 | Robinson |
| 2012/0330422 A1 | 12/2012 | Weiman |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0190876 A1* | 7/2013 | Drochner ............ A61F 2/4455<br>623/17.16 |
| 2013/0211526 A1 | 8/2013 | Alheidt et al. |
| 2014/0148904 A1 | 5/2014 | Robinson |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |

(56) References Cited

U.S. PATENT DOCUMENTS

| | | |
|---|---|---|
| 2014/0343678 A1 | 11/2014 | Suddaby et al. |
| 2015/0066145 A1 | 3/2015 | Rogers et al. |
| 2015/0100128 A1 | 4/2015 | Glerum et al. |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0120660 A1* | 5/2016 | Melkent ............ A61F 2/447 623/17.16 |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2017/0056197 A1 | 3/2017 | Weiman et al. |
| 2017/0172756 A1 | 6/2017 | Faulhaber |
| 2017/0189200 A1* | 7/2017 | Miller ............ A61F 2/447 |
| 2017/0216036 A1 | 8/2017 | Cordaro |
| 2017/0216045 A1 | 8/2017 | Dewey et al. |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1* | 11/2017 | Robinson ............ A61F 2/4455 |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0185164 A1* | 7/2018 | Sharabani ............ A61F 2/4425 |
| 2018/0243107 A1 | 8/2018 | Foley et al. |
| 2018/0256359 A1 | 9/2018 | Greenhalgh |
| 2018/0296361 A1* | 10/2018 | Butler ............ A61F 2/4455 |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360615 A1 | 12/2018 | Miller et al. |
| 2018/0360616 A1 | 12/2018 | Luu |
| 2019/0021871 A1 | 1/2019 | Baynham |
| 2019/0133779 A1 | 5/2019 | McLaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0281741 A1* | 9/2020 | Grotz ............ A61F 2/447 |
| 2021/0015627 A1 | 1/2021 | Weiman et al. |
| 2021/0045892 A1 | 2/2021 | Rogers et al. |
| 2021/0137699 A1* | 5/2021 | Jang ............ A61F 2/447 |
| 2021/0196469 A1 | 7/2021 | Caratsch |
| 2021/0259849 A1 | 8/2021 | Robinson et al. |
| 2021/0275318 A1* | 9/2021 | Reimels ............ A61F 2/4455 |
| 2022/0133495 A1 | 5/2022 | Glerum et al. |
| 2022/0296385 A1* | 9/2022 | Predick ............ A61F 2/447 |

FOREIGN PATENT DOCUMENTS

| | | |
|---|---|---|
| DE | 94 07 806 U1 | 7/1994 |
| EP | 0 880 950 A1 | 12/1998 |
| EP | 2 777 633 A2 | 9/2014 |
| EP | 3 031 424 A1 | 6/2016 |
| EP | 3 245 982 | 11/2017 |
| EP | 3 479 799 A1 | 5/2019 |
| FR | 2717068 A1 | 4/1996 |
| FR | 2727003 B1 | 4/1997 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 | 6/2004 |
| WO | WO-2005/009299 A1 | 2/2005 |
| WO | WO-2006/102485 | 9/2006 |
| WO | WO-2006/105437 A2 | 10/2006 |
| WO | WO-2009/124269 A1 | 10/2009 |
| WO | WO-2010/148112 | 12/2010 |
| WO | WO-2014/134590 A1 | 9/2014 |
| WO | WO-2014/165319 A1 | 10/2014 |
| WO | WO-2015/063721 A1 | 5/2015 |
| WO | WO-2015/085111 A1 | 6/2015 |
| WO | WO-2016/077610 A1 | 5/2016 |
| WO | WO-2016/127139 A1 | 8/2016 |
| WO | WO-2017/027277 A1 | 2/2017 |
| WO | WO-2017/027873 A1 | 2/2017 |
| WO | WO-2017/066463 A1 | 4/2017 |
| WO | WO-2018/049227 A1 | 3/2018 |
| WO | WO-2018/200507 A1 | 11/2018 |
| WO | WO-2019/014139 A1 | 1/2019 |
| WO | WO-2019/241687 A1 | 12/2019 |

OTHER PUBLICATIONS

International Search Report and Written Opinion on PCT PCT/US2021/049280 dated Jan. 11, 2022 (12 pages).

Schizas, C., "Spinal Fusion: Techniques Results and Limitations." European Cells and Materials. 2005, vol. 10, Suppl. 3, p. 1.

"MectaLIF Oblique & Posterior Intervertebral Body Fusion Device." Brochure. 2004, Medacta International, San Pietro, Switzerland.

"Webster's II New College Dictionary." Excerpts. 2005, Houghton Mifflin Co., p. 992.

"Wedge." Encyclopedia Brittanica. Aug. 14, 2008. britannica.com/print/article/638734.

Kambin, P., et al., "Arthroscopic Discectomy of the Lumbar Spine." Clinical Orthopaedics and Related Research. Apr. 1997, No. 337, pp. 49-57.

Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.

Kim, Y, et al., "Clinical Applications of the Tubular Retractor on Spinal Disorders." Journal of Korean Neurosurgery, Nov. 2007, No. 42, pp. 244-250.

Moore, J., et al., "Mechanics Map—Wedges." Aug. 20, 2022, mechanicsmap.psu.edu/websites/7_friction/7-3_wedges/wedges.

Peltier, L. "Orthopedics: A History and Iconography" 1993, Norman Publishing, San Francisco, CA.

Sasso, R., et al., "Anterior Lumbar Interbody Fusion." Surgical Management of Low Back Pain. 2009, Chapter 10, pp. 87-95.

Tsuang, Y., et al., "Comparison of cage application modality in posterior lumbar interbody fusion with posterior instrumentation—A finite element study." Medical Engineering & Physics 31. 2009, pp. 565-570.

Virk, S., et al. "History of Spinal Fusion: Where We Came from and Where We Are Going." Current Concepts in Spinal Fusion. HSS Journal, 2020, No. 16, pp. 137-142.

Xiao, Y, et al., "Unilateral Transforaminal Lumbar Interbody Fusion: a Review of the Technique, Indications and Graft Materials." The Journal of International Medical Research. 2009, No. 37, pp. 908-917.

* cited by examiner

EXPANDABLE IMPLANT WITH PIVOTING CONTROL ASSEMBLY

This application is a continuation of application Ser. No. 17/014,546, filed Sep. 8, 2020, which is incorporated herein by reference in its entirety.

BACKGROUND

The present disclosure relates generally to expandable implants usable in connection with the spine or other parts of the human anatomy. Certain implants are expandable, in that the implants may, for example, have a variable height dependent upon a degree of expansion.

SUMMARY

At least one embodiment relates to an expandable implant. The expandable implant includes a lower support; an upper support pivotally coupled to the lower support and including a control channel; and a control assembly. The control assembly includes a control shaft coupled to the lower support; and a control member coupled to the control shaft and configured to move along the control shaft. The control member includes a base member and a pivot member pivotally coupled to the base member, the pivot member configured to move within the control channel. Movement of the control member along the control shaft causes the pivot member to pivot relative to the base member, and the upper support to pivot relative to the lower support.

Another embodiment relates to an expandable implant. The expandable implant includes a first support; an second support pivotally coupled to the first support; a control shaft rotatably coupled to the first support; and a control member coupled to the control shaft and configured to move along the control shaft such that movement of the control member along the control shaft cause pivotal movement of the second support relative to the first support, a portion of the control member configured to rotate relative to the second support as the control member moves along the control shaft.

Another embodiment relates to an expandable implant. The implant includes a lower support having a first lower surface, a first upper surface, an access bore configured to receive an expansion tool, and an inner housing that defines a central aperture extending between the first lower surface and the first upper surface, an upper support having a second upper surface, a second lower surface, a control channel, and a rear aperture extending between the second upper surface and the second lower surface, wherein the upper support is pivotally coupled to the lower support, the implant is configured to expand between a first, collapsed position and a second, expanded position such that pivotal movement of the upper support relative to the lower support changes an angle defined between the first lower surface and the second upper surface as the implant expands, and at least a portion of the inner housing is received by the rear aperture the first, collapsed position, a control shaft rotatably coupled to the lower support, wherein the control shaft includes a head configured to receive the expansion tool, wherein manipulation of the expansion tool causes the implant to expand, and wherein the central aperture is located between the head and the access bore, and a control member threadingly coupled to the control shaft, the control member includes a base member threadingly coupled to the control shaft and rotatably fixed relative to the lower support, a first pivot member pivotally coupled to a first side of the base member and slidingly received in the control channel, a second pivot member pivotally coupled to a second side of the base member opposite the first side and slidingly received in the control channel.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
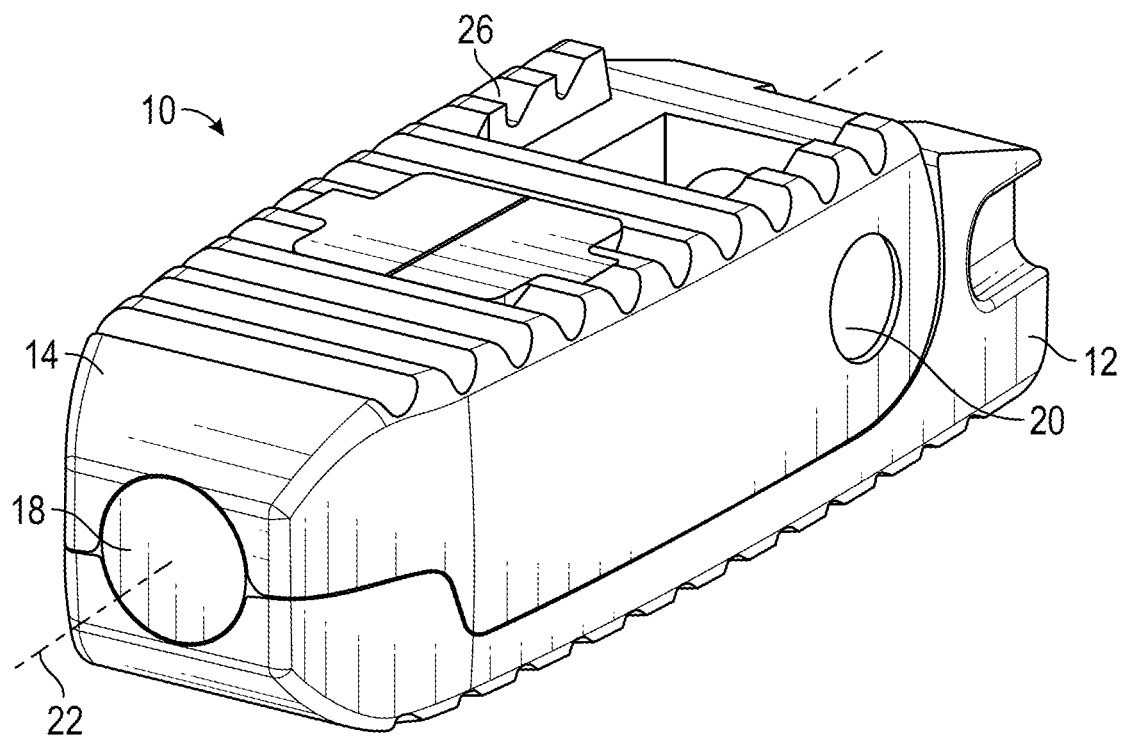
FIG. 1 is a perspective view of an implant in a collapsed position according to one embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, various embodiments of an expandable implant are disclosed herein. The expandable implant may be usable in connection with the spine (e.g., between vertebral bodies) or other parts of the human body. In some embodiments, the implant provides a lumbar interbody expandable implant that expands in a lordotic fashion. The implant may include an upper support hingedly or pivotally coupled to a lower support, such that an amount of lordosis provided by the implant can be adjusted as desired. A control assembly may include a control shaft and a control member mounted to the control shaft. One or more pivoting members are pivotally coupled to the control member and move within one or more control channels in the upper implant. In one embodiment, rotation of the control shaft causes translation of the control member along the control shaft relative to the lower support. As the control member translates, ramp surfaces on the pivoting member(s) slidingly engage corresponding ramp surface(s) on the upper support to cause expansion or contraction of the implant (e.g., to move the implant between a collapsed position and an expanded position, and intermediate positions therebetween).

The implants disclosed herein may be made of any suitable materials, including a variety of metals, plastics, composites, or other suitable bio-compatible materials. In some embodiments, some or all of the components of the implants disclosed herein may be made of the same material, while in other embodiments, different materials may be used for different components.

Referring now to FIGS. 1-8, an expandable implant 10 is shown according to one embodiment. Implant 10 is usable, for example, between and/or within portions of bone (e.g., between and/or within vertebral bodies or the spine or other portions of bone). In one embodiment, implant 10 includes a lower support 12 (e.g., a base support or assembly, a foundational plate, endplate, or member, etc.) and an upper support 14 (e.g., an adjustable support or assembly, a hinged plate, endplate, or member, etc.) adjustably coupled to the lower support 12 by way of a control assembly 16 (e.g., an adjustment assembly, etc.) and one or more pivot pins 20. In some embodiments, upper support 14 pivots relative to lower support 12 as a result of user manipulation of control assembly 16 (e.g., as a result of rotation or movement of a control shaft or member, etc.). In one embodiment, upper support 14 expands relative to lower support 12 in a lordotic fashion to mimic the natural curvature of the human spine. The amount of lordosis can be increased or decreased by manipulation of control assembly 16. An end cap 18 (e.g., a distal end member, etc.) assists in maintaining control assembly 16 in a desired position. Pivot pins 20 extend at least partially through lower support 12 and upper support 14 to enable relative pivoting adjustment between upper support 14 and lower support 12.

Figure 2:
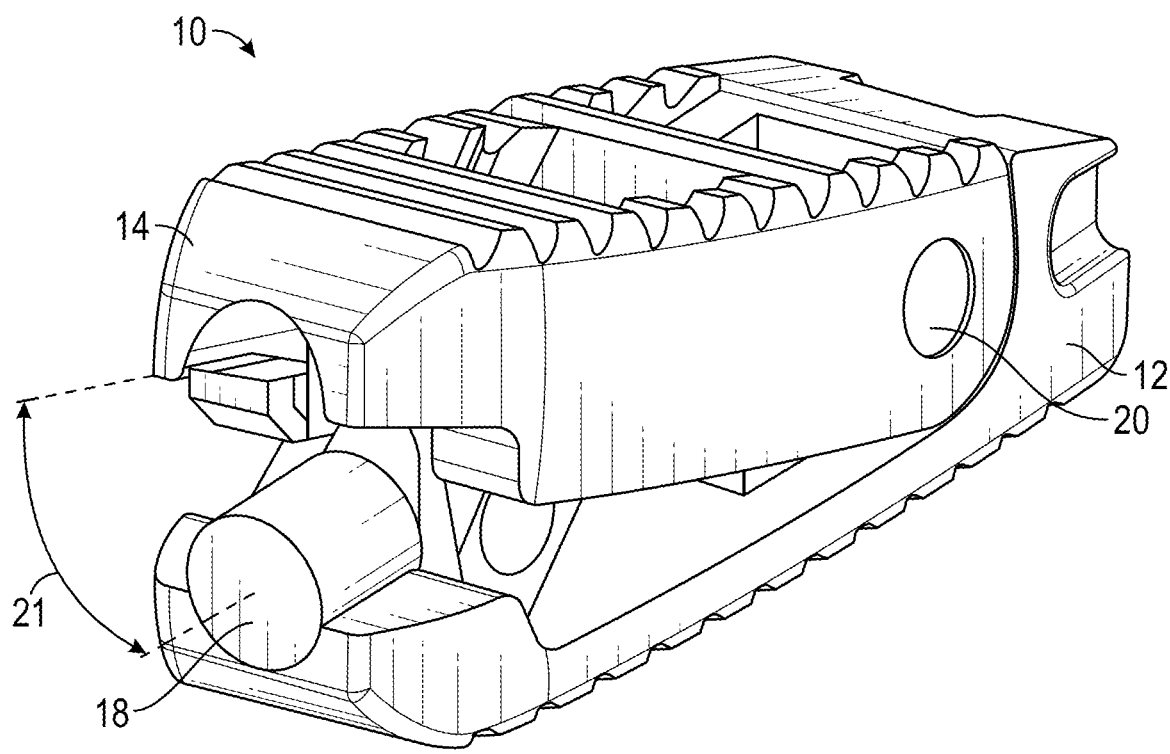
FIG. 2 is a perspective view of the implant of FIG. 1 in an expanded position according to one embodiment.
Figure 3:
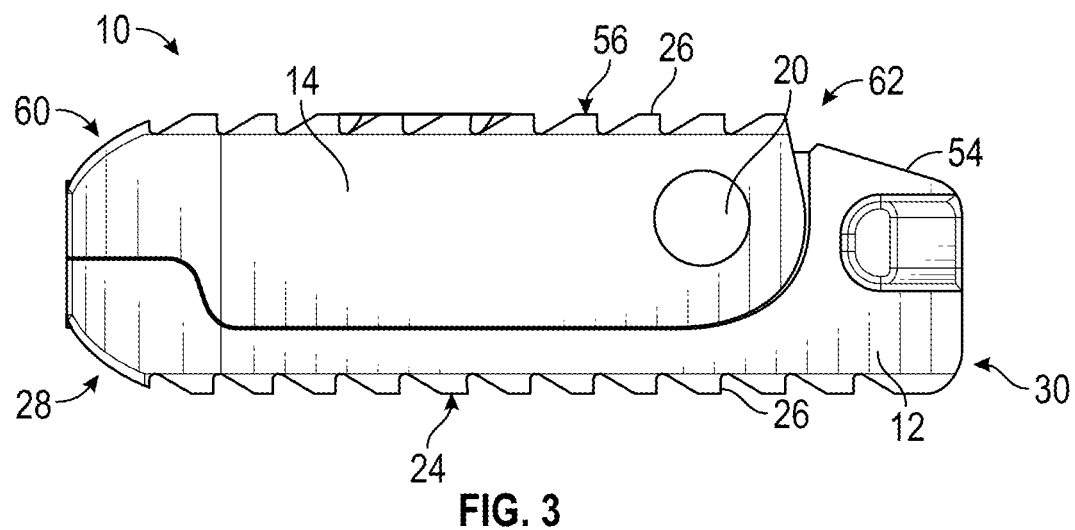
FIG. 3 is a side view of the implant of FIG. 1 in the collapsed position according to one embodiment.
Figure 4:
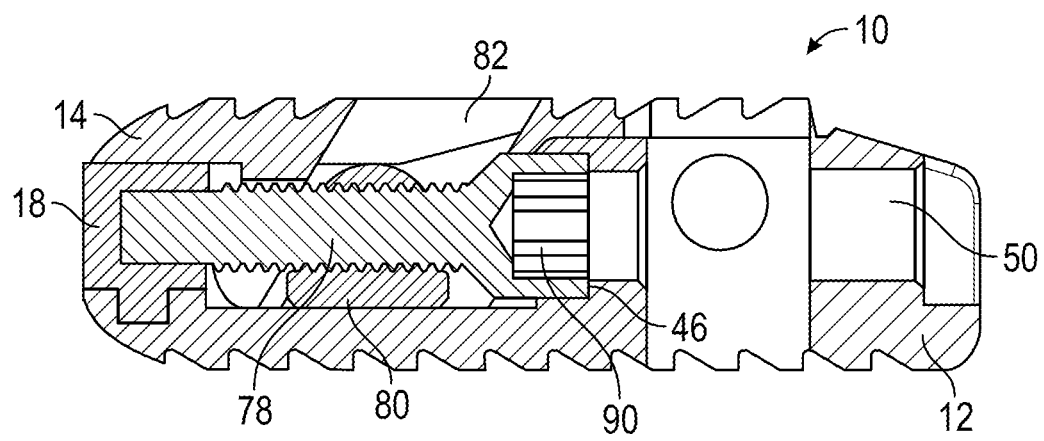
FIG. 4 is a cross-section view of the implant of FIG. 1 in a collapsed position according to one embodiment.
Figure 5:
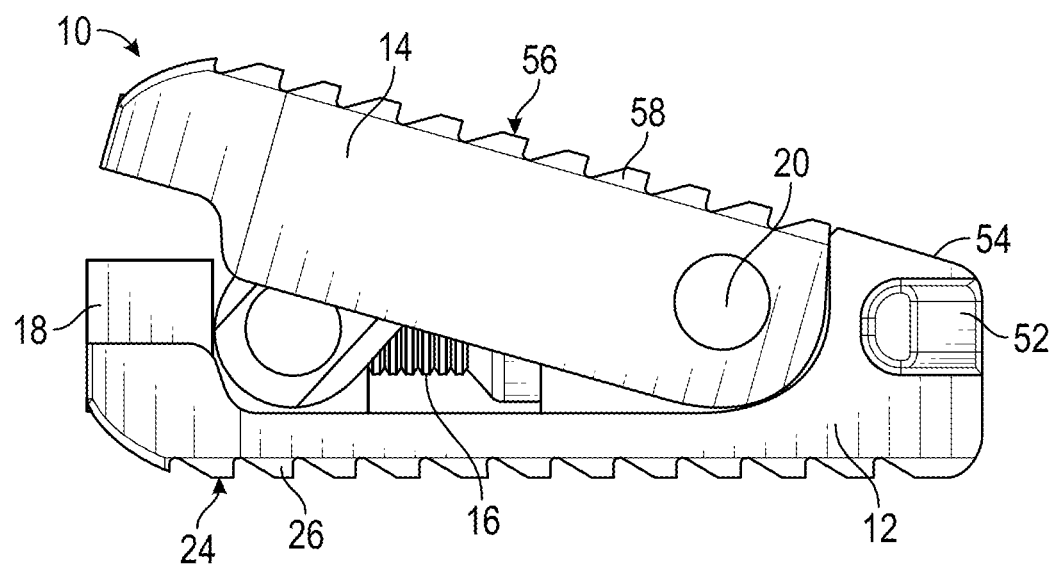
FIG. 5 is a side view of the implant of FIG. 1 in an expanded position according to one embodiment.
Figure 6:
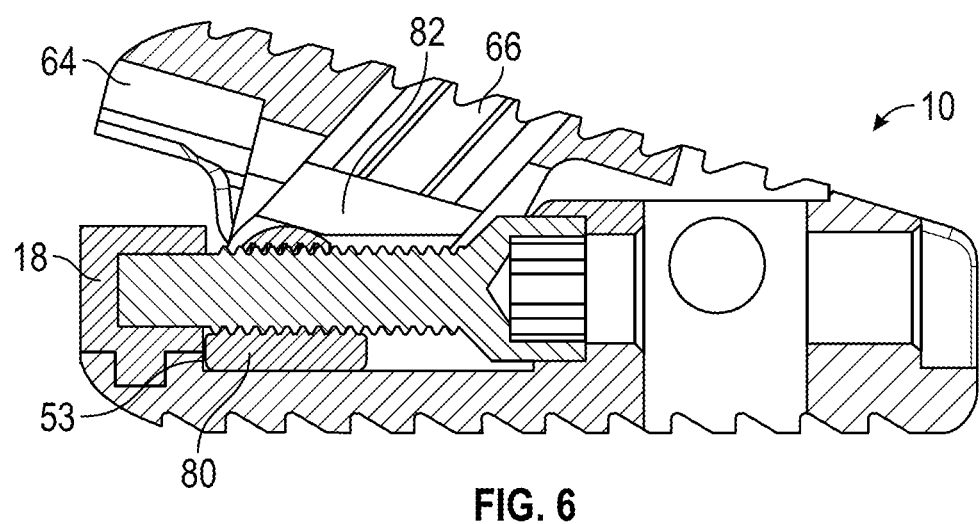
FIG. 6 is a side view of the implant of FIG. 1 in an expanded position according to one embodiment.
Figure 7:
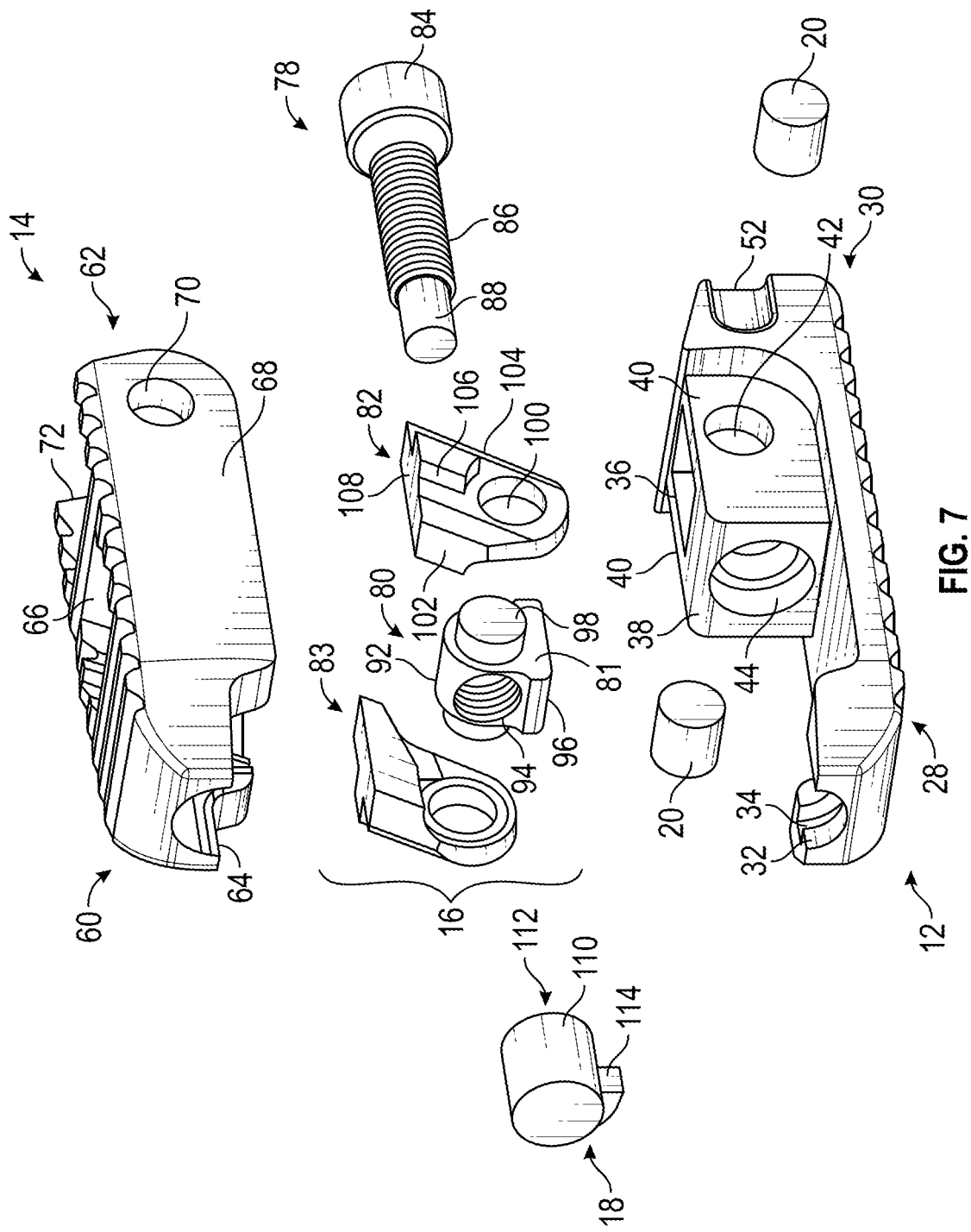
FIG. 7 is an exploded view of the implant of FIG. 1 according to one embodiment.
Figure 8:
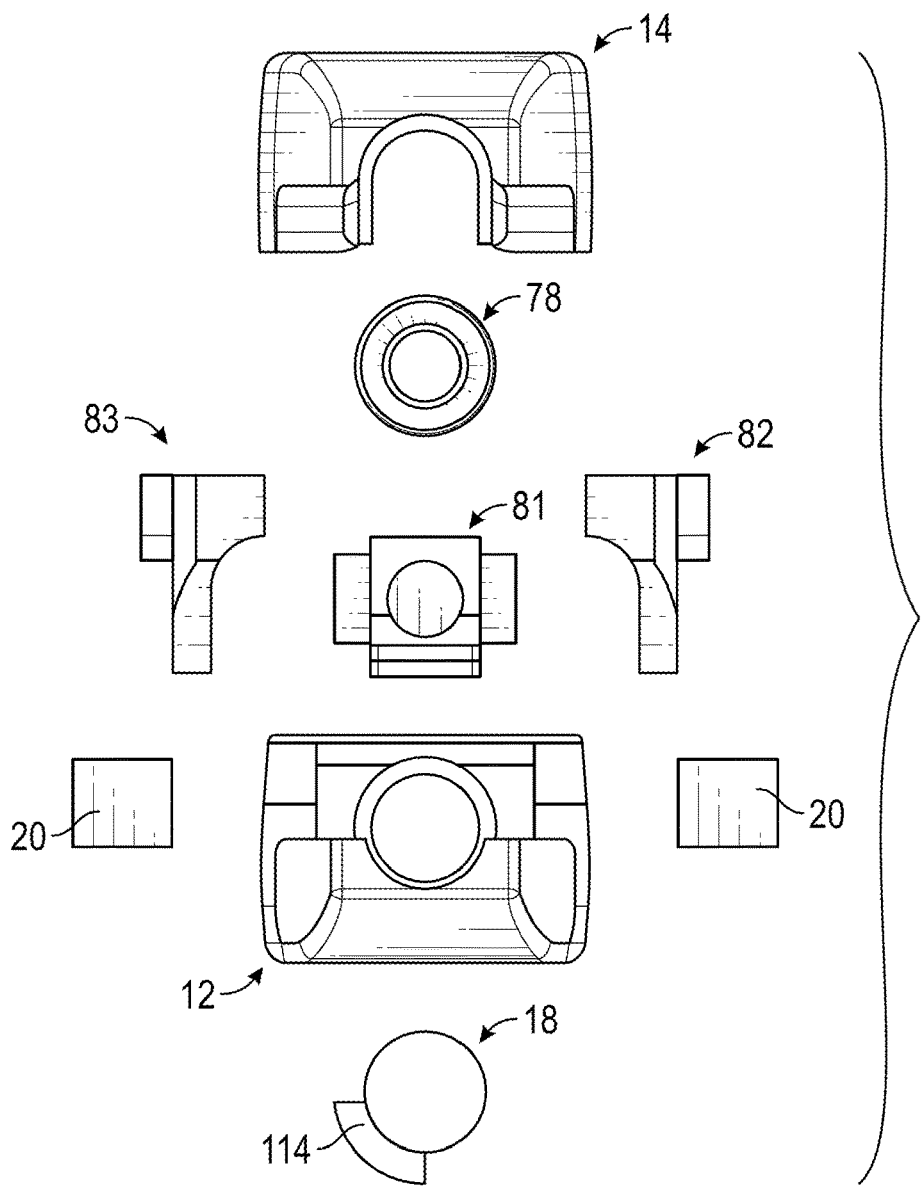
FIG. 8 is another exploded view of the implant of FIG. 1 according to one embodiment.

Implant 10 is movable between a collapsed position, as shown, for example, in FIGS. 1, 3, and 4, and an expanded position, as shown, for example, in FIGS. 2, 5, and 6. Further, implant 10 may be adjusted to any intermediate position between a fully collapsed position and a fully expanded position. Further yet, the amount of total expansion, (e.g., the maximum expansion angle 21 relative to axis 22 shown in FIGS. 1 and 2) may be varied to suit a particular application.

According to one embodiment, lower support 12 extends between a distal end 28 and a proximal end 30 and includes a bottom surface 24 having a plurality of ridges 26 (e.g., teeth, etc.) formed by corresponding grooves or channels. Ridges 26 are configured to facilitate gripping of adjacent portions of bone. A lower distal recess 32 is provided at distal end 28, and a retention groove 34 extends from lower distal recess 32. Retention groove 34 is configured to receive a retention projection 114 of end cap 18, as discussed in greater detail elsewhere herein. In some embodiments, lower support 12 includes an inner housing 36. Inner housing 36 is defined by a front wall 38 and side walls 40 that extend from front wall 38 toward proximal end 30 of lower support 12. Inner housing 36 in some embodiments defines a central aperture 48 (e.g., a cavity, etc.) providing access to an interior of implant 10. Central aperture 48 may be configured to receive bone growth material and/or bone material from adjacent portions of bone.

Lower support 12 further includes an access bore 50, tool recesses 52, and an inclined surface 54. Access bore 50 (see FIG. 4) provides access to central aperture 48 (e.g., for delivery of bone growth or other material) and control assembly 16 (e.g., to enable manipulation of control assembly 16 and control of the expansion and/or contraction of implant 10). Tool recesses 52 are configured to receive one or more tool portions to enable positioning of implant 10 in a desired position (e.g., within an intervertebral space, etc.). Inclined surface 54 (see FIG. 5) is in one embodiment configured such that when implant 10 is in an expanded configuration, inclined surface 54 is aligned with (e.g., substantially coplanar with) a top surface 56 of upper support 14 to provide additional support to adjacent portions of bone. In some embodiments, inclined surface 54 is angled downward in a proximal direction relative to a top surface 56 of upper support 14 when implant 10 is in a collapsed position. The angular position of inclined surface 54 is in some embodiments intended to accommodate the natural curvature of the human spine.

According to one embodiment, upper support 14 extends between a distal end 60 and a proximal end 62 and includes a top surface 56 having a plurality of ridges 58 (e.g., teeth, etc.) formed by corresponding grooves or channels. Ridges 58 are configured to facilitate gripping of adjacent portions of bone. An upper distal recess 64 is provided at distal end 60 and receives end cap 18. Sidewalls 68 extend downward relative to top surface 56.

In one embodiment, upper support 14 includes two opposing sidewalls 68. Each sidewall 68 includes a pivot pin aperture 70 configured to receive a pivot pin 20 there through to enable pivoting movement of upper support 14 relative to lower support 12. Upper support 14 also includes a rear aperture or cavity 72 that receives all or a portion of inner housing 36 when implant 10 is a collapsed position. A control aperture 66 extends through upper support 14 and is defined at least partially by distal ramp surfaces 74 and proximal ramp surfaces 76. An alignment channel 77 extends along each sidewall 68 and along control aperture 66. As discussed in further detail below, control aperture 66 receives portions of control assembly 16, and the angle of control aperture 66 relative to axis 22 may be designed to provide a desired rate of pivoting of upper support 14 relative to lower support 12.

In one embodiment, control assembly 16 includes a control shaft 78, a control member 80, and one or more pivot members 82. In some embodiments, control assembly 16 includes a pair of pivot members 82, 83 positioned on opposite sides of control member 80. Control shaft 78 is rotatable or otherwise manipulatable to cause translation or movement of control member 80 along control shaft 78. As control member 80 moves along control shaft 78, pivot members 82 move within control aperture 66 (see FIG. 6) to change the angular position of upper support 144 relative to lower support 12.

Control shaft 78 includes a head 84, a threaded portion 86, an end portion 88 and a receiver 90 provided in head 84. Head 84 defines a first end of control shaft 78 and end portion 88 defines a second opposite end of control shaft 78, with threaded portion 86 provided there between. Head 84 is received in a control member bore 44 and engages a shoulder 46 to limit proximal movement of control shaft 78 during use of implant 10. End portion 88 is received by end cap 18 to limit distal movement of control shaft 78.

Control member 80 is received on control shaft 78. In one embodiment, control member 80 includes a base member 81 and one or more pivot members 82. In some embodiments, control member 80 includes first and second pivot members 82, 83 pivotally coupled to opposite sides of base member 81.

Base member 81 includes a central portion 92 having a threaded bore 94 that threadingly engages threaded portion 86 of control shaft 78. Base member 81 further includes a bottom 96 and a pair cylindrical pivot bosses 98. Due to the threaded engagement of base member 81 onto control shaft 78, rotation of control shaft 78 causes movement (e.g., translational movement) of base member 81 along control shaft 78.

In one embodiment, each pivot member 82, 83 includes a pivot aperture 100 that receives one of the pivot bosses 98 to enable pivoting movement of pivot members 82, 83 relative to base member 81 about pivot bosses 98. Pivot member 82, 83 are mirror images of each other in one embodiment, and as such, pivot member 82 will be described in detail, with the understanding that pivot member 83 shares similar features. For example, pivot member 83 may include an alignment guide 107 that is similar to alignment guide 106.

Pivot member 82 includes distal ramp surface 102, proximal ramp surface 104, alignment guide 106, and top surface 108. Distal ramp surface 102 of pivot member 82 slidingly engages distal ramp surface 74 of upper support 14. Similarly, proximal ramp surface 104 of pivot member 82 slidingly engages proximal ramp surface 76 of upper support 14. During movement of base member 81 along control shaft 78, pivot members 82, 83 pivot about pivot bosses 98 as the corresponding distal and proximal ramp surfaces of the pivot members 82, 83 and upper support 14 engage, causing upper support 14 to move relative to lower support 12, and implant 10 to move toward an expanded or collapsed position, depending on the direction of rotation of control shaft 78.

Alignment guide 106 of pivot member 82 is received within alignment channel 77 of upper support 14 to maintain proper alignment between components and facilitate movement of upper support 14 relative to lower support 12. In some embodiments, when implant 10 is in a collapsed position, top surface 108 of pivot member 82 is generally aligned with top surface 56 of upper support 14. In some embodiments, top surface 108 may be substantially smooth, while in other embodiments, top surface 108 may be textured, include teeth or groves, or have other surface features.

End cap 18 includes a main body 110, a control shaft bore 112, and a retention projection 114. Control shaft bore 112 receives end portion 88 of control shaft 78. Retention projection 114 is received in retention groove 34 in lower support 12 to retain end cap 18 in place. In one embodiment, end cap 18 is rotated approximately 90 degrees to properly seat retention projection 114 within retention groove 34.

According to one embodiment, during use, a user positions implant 10 into a desired position, such as an intervertebral space, while collapsed, as shown, for example, in FIG. 1. To reposition implant 10, an appropriate tool may engage tool recesses 52 on lower support 12. In some embodiments, implant 10 is inserted into a space distal end first, with the appropriate tool engaging the proximal end of implant 10.

If desired, implant 10 may then be expanded to provide, for example, a desired amount of lordosis. Implant 10 may be expanded to a fully expanded position, or any intermediate expanded position between the fully collapsed position and the fully expanded position. In order to expand implant 10, in some embodiments, a user inserts an appropriate expansion tool through access bore 50 in lower support 12 and into receiver 90 in head 84 of control shaft 78. The expansion tool may then be used to manipulate the control shaft 78 to cause expansion of the implant 10. For example, receiver 90 may be hexagonal shaped, and the tool may be a hexagonal driver. Other suitable receivers and tools may be used according to various alternative embodiments.

As control shaft 78 is rotated, control member 80 translates along control shaft 78. For example, in one embodiment, to expand implant 10, control member 80 moves toward the distal end of lower support 12 as shown in FIGS. 4 and 6. Bottom 96 of base member 80 rides along a surface of lower support 12, and the travel of control member 80 is limited by limit shoulder 53, as shown in FIG. 6. In some embodiments, shoulder 53 is integrally formed (e.g., molded, etc.) with a remaining portion of lower support 12 to provide sufficient support for control shaft 78 during expansion of implant 10.

As control member 80 moves along control shaft 78, ramp surfaces on pivot members 82, 83 engage ramp surfaces of upper support 14 and cause upper support 14 to rotate about pivot pins 20. As upper support 14 pivots relative to lower support 12, pivot members 82 pivot about pivot bosses 98 on base member 81 to maintain proper alignment between the ramp surfaces on pivot members 82, 83 and the ramp surfaces on upper support 14.

In some embodiments and as shown in the FIGURES, the pivoting features of upper support 14 and pivot members 82, 83 maintain a generally parallel relationship between ramp surfaces 74, 76 of upper support 14 and ramp surfaces 102, 104 of pivot members 82, 83, which may facilitate the wedging action required to move upper support 14 relative to lower support 12.

If it is desirable to move implant 10 toward the collapsed position, control shaft 78 is rotated in an opposite direction from that used during expansion of implant 10. In one embodiment, to collapse implant 10, control member 80 moves toward the proximal end of lower support as shown in FIGS. 4 and 6. As control member 80 moves along control shaft 78, ramp surfaces on pivot members engage ramp surfaces of upper support 14 and cause upper support 14 to rotate about pivot pins 20.

Figure 9:
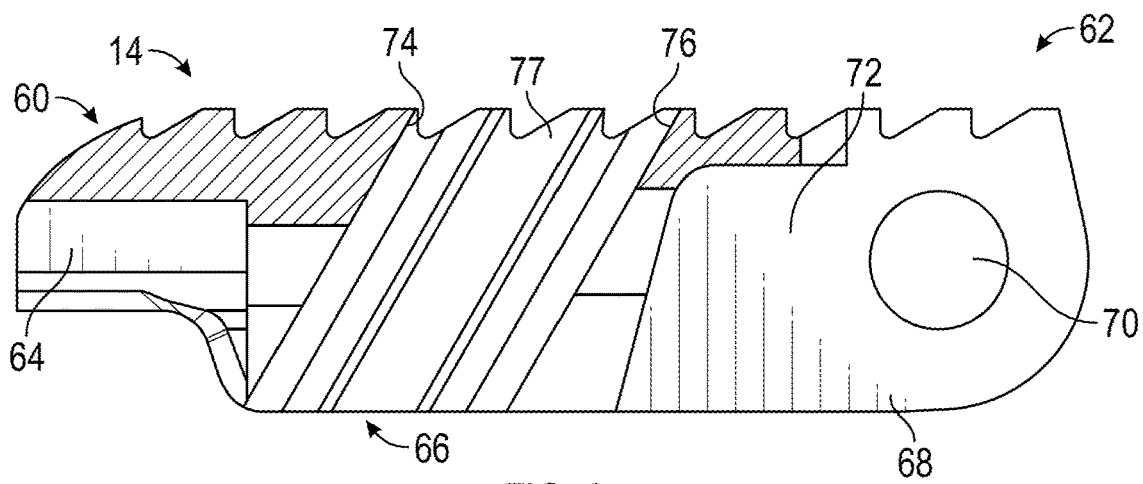
FIG. 9 is a side cross-section view of an upper support of the implant of FIG. 1 according to one embodiment.

Referring now to FIG. 9, a cross-section view of the upper support 14 is shown according to an example embodiment. As shown, the upper support 14 includes a control aperture 66 configured to receive the pivot member 83. For example, the alignment guide 107 of the pivot member 83 may slide within the alignment channel 77 of the control aperture 66 as the implant 10 expands. Further, the distal ramp surface 74 and the proximal ramp surface 76 may interface with the ramp surfaces of the pivot member 83 when the implant 10 expands. The angle of expansion (e.g., angle 21) and the rate of angular expansion may be customized by altering the angles of the ramp surfaces 74, 76 and the alignment channel 77. It should be appreciated that the upper support 14 may also include a second control aperture 77 opposite the control aperture 66 configured to receive the pivot member 82 in a similar manner (see FIG. 10). The upper support 14 is also shown include a pivot pin aperture 70 configured to receive a pivot pin 20 there through to enable pivoting movement of upper support 14 relative to lower support 12.

Figure 10:
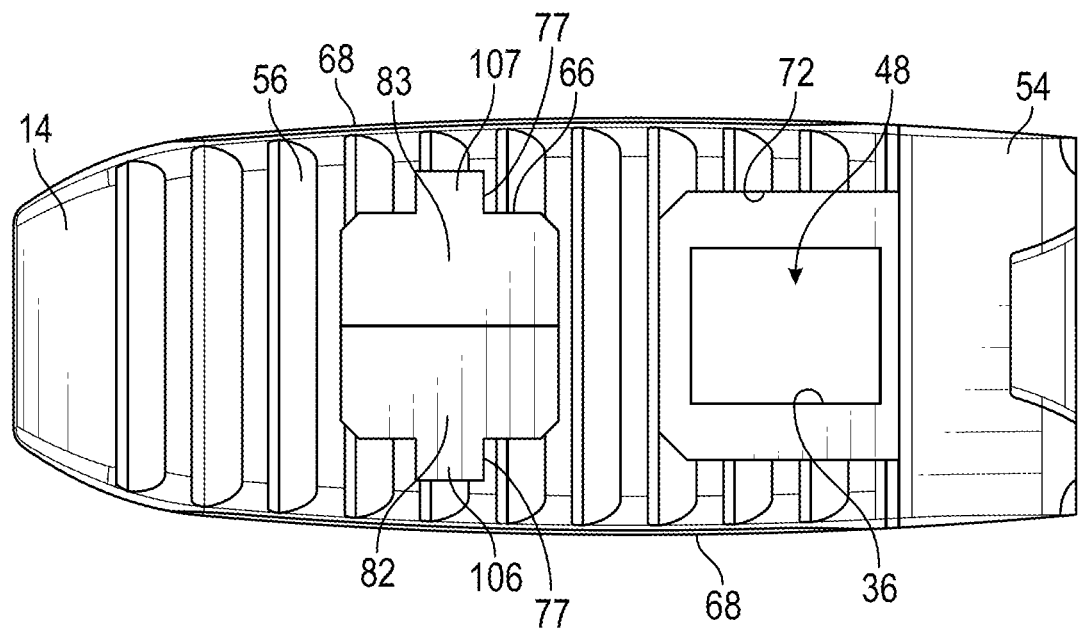
FIG. 10 is a top view of the implant of FIG. 1 according to one embodiment.
Figure 11:
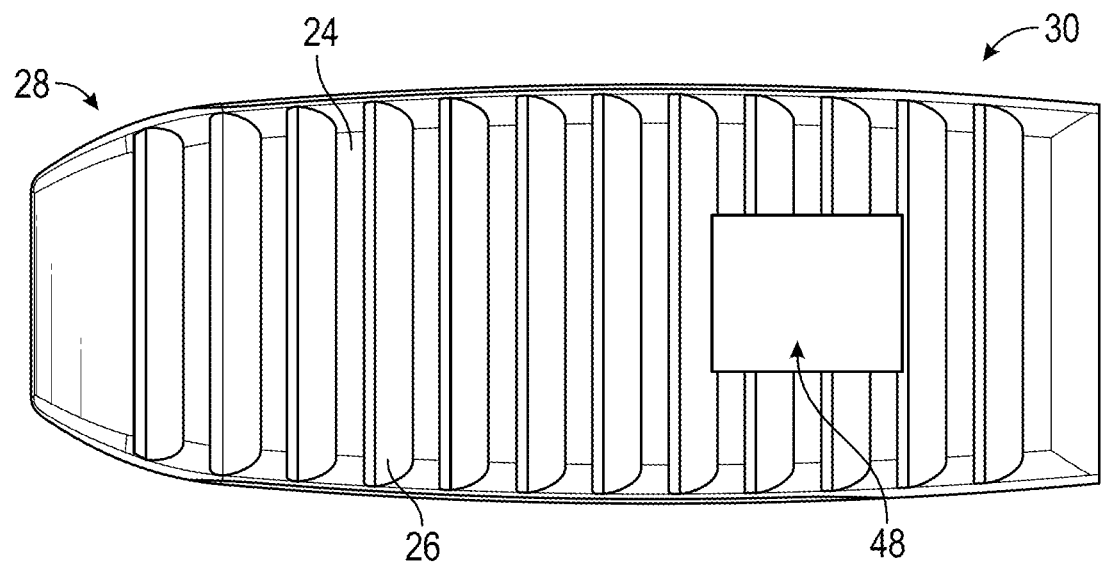
FIG. 11 is a bottom view of the implant of FIG. 1 according to one embodiment.

Referring now to FIGS. 10 and 11, a top view and a bottom view, respectively, of the implant 10 is shown according to an example embodiment. As shown, pivot member 83 includes an alignment guide 107 that is received by the first alignment channel 77 in the upper support 14. Further, pivot member 82 includes an alignment guide 106 that is received by the second alignment channel 77 in the upper support. Further, as shown, the rear aperture 72 of the upper support 14 also receives all or a portion of the inner housing 36. The inner housing 36 further defines the central aperture 48 (e.g., a cavity, etc.) providing access to an interior of implant 10 from the top surface 56 of the upper support and from the bottom surface 24 of the lower support 12. Central aperture 48 may be configured to receive bone growth material and/or bone material from adjacent portions of bone.

Figure 12:
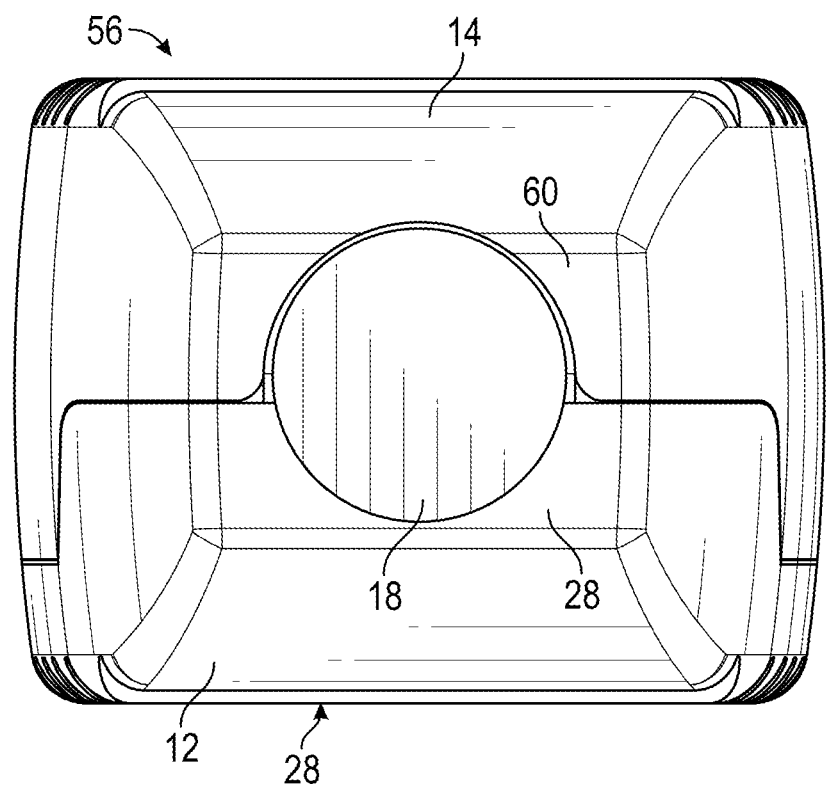
FIG. 12 is a front view of the implant of FIG. 1 according to one embodiment.
Figure 13:
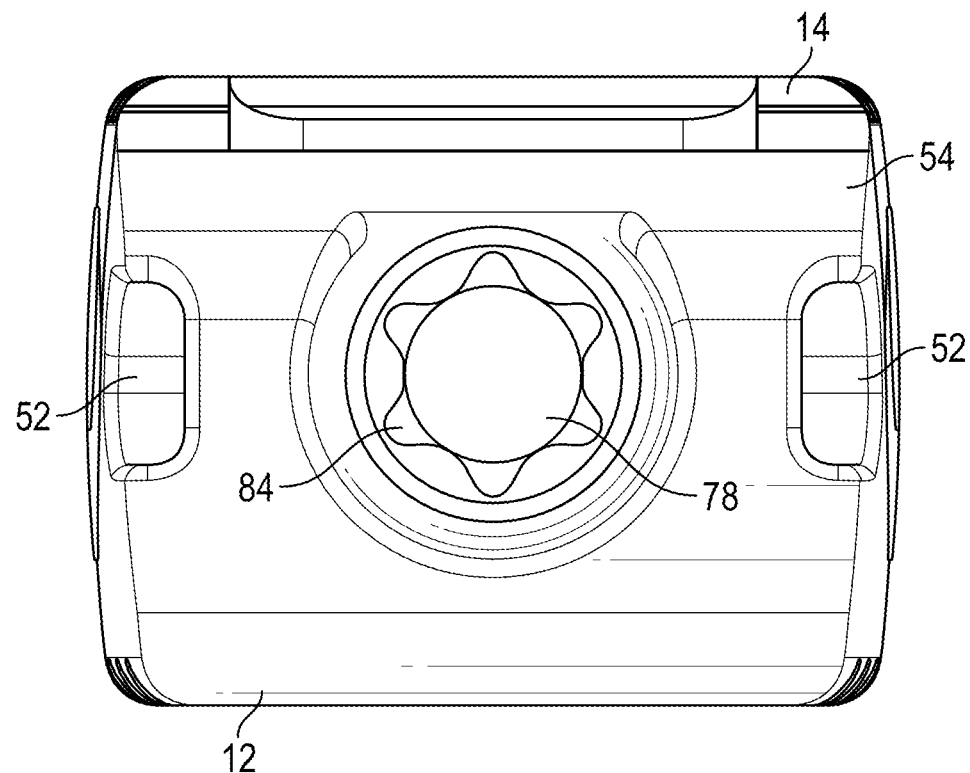
FIG. 13 is a rear view of the implant of FIG. 1 according to one embodiment.

Referring now to FIGS. 12 and 13, a front and rear view, respectively, of the implant 10 are shown. As shown, in the collapsed position, the upper support 14 and the lower support 12 form a bull shaped nose that receives the end cap 18 at the front of the implant 10. The bull shaped nose all the implant 10 to be inserted into a desired location before the implant 10 is expanded. As shown in FIG. 13, the control shaft 78 is received by the rear of the implant 10. However, in operation, the head 84 is positioned away from the rear end of the implant 10, and is at least partially received by the control member bore 44 in the lower support 12.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. All such variations are within the scope of the disclosure.

It is important to note that the construction and arrangement of the expandable implant as shown in the various exemplary embodiments is illustrative only. Additionally, any element disclosed in one embodiment may be incorporated or utilized with any other embodiment disclosed herein. It should be appreciated that elements of the various embodiments may be incorporated or utilized with any of the other embodiments disclosed herein.

What is claimed is:

1. An expandable implant comprising:
    a first support comprising a first surface configured to engage bone;
    a second support movably coupled to the first support and comprising a control aperture and a second surface opposite the first surface and configured to engage bone, wherein the control aperture is defined by the second support and extends through the second surface; and
    a control assembly comprising:
        a control shaft; and
        a control member threadingly received on the control shaft and configured to translate along the control shaft, wherein the control member comprises a base member and a pair of pivot members pivotally coupled to the base member, wherein ramp surfaces of the pivot members are configured to engage ramp surfaces defining the control aperture to move the pivot members within the control aperture;
    wherein translation of the base member along the control shaft causes the pivot members to pivot relative to the base member, and the first support to move relative to the second support to change an angle between the first surface and the second surface.

2. The expandable implant of claim 1, wherein the first support and the pivot members are aligned via an interface comprising an alignment projection slidably received in an alignment channel.

3. The expandable implant of claim 1, wherein the pair of pivot members comprise first and second pivot members independently coupled and rotatable to opposite sides of the base member.

4. The expandable implant of claim 3, wherein the first pivot member is received on a first boss on a first side of the base member and the second pivot member is received on a second boss on a second side of the base member.

5. The expandable implant of claim 1, wherein the first surface is generally parallel to the second surface when the expandable implant is in a collapsed position.

6. The expandable implant of claim 1, wherein the second support comprises an inner housing defining a cavity and providing access to an interior of the expandable implant.

7. The expandable implant of claim 6, wherein the second support defines an access bore providing tool access to the control shaft via the access bore and the cavity, wherein the cavity is located between the access bore and the control shaft.

8. The expandable implant of claim 6, wherein the control shaft comprises a head received by the inner housing.

9. An expandable implant comprising:
a first support comprising opposing sidewalls and a first exterior surface, the sidewalls each comprising an interior ramped surface, the first exterior surface configured to engage bone;
a second support coupled to the first support and comprising a second exterior surface opposite the first exterior surface and configured to engage bone;
a control shaft rotatably coupled to the first support; and
a control member coupled to the control shaft and comprising a base member and a pair of pivot members rotatably coupled to the base member, the base member configured to move relative to the control shaft and cause the second support to pivot relative to the first support, wherein the pivot members each comprise a first ramp surface and a second ramp surface configured to engage the interior ramped surfaces of the first support, and wherein the pivot members are configured to rotate relative to the second support and translate relative to the first support as the control member moves relative to the control shaft.

10. The expandable implant of claim 9, wherein the pivot members are coupled to opposite sides of the base member.

11. The expandable implant of claim 10, wherein the second support comprises a shoulder portion configured to engage the control member to limit an amount of travel of the control member and an amount of movement of the first support relative to the second support.

12. The expandable implant of claim 9, wherein the second support comprises a housing defining a cavity and a control member bore, wherein the control member bore receives a head of the control shaft.

13. The expandable implant of claim 12, wherein the base member is threadingly received on a threaded portion of the control shaft, and wherein the cavity is positioned on an opposite side of the head of the control shaft from the threaded portion.

14. An expandable implant comprising;
a first support defining a control aperture wherein the control aperture extends through a surface of the first support configured to engage bone;
a second support coupled to the first support;
a control shaft rotatably coupled to the first support; and
a control member coupled to the control shaft and comprising a base member and a pivot member, the base member configured to move relative to the control shaft and cause pivotal movement of the pivot member relative to the base member and the second support relative to the first support, the pivot member configured to rotate relative to the second support and translate relative to the first support as the control member moves relative to the control shaft,
wherein the control shaft comprises an end portion rotatably received by the end cap, a head portion rotatably received by the second support, and a threaded portion between the end portion and the head portion.

15. An expandable implant comprising:
a lower support comprising a first lower surface, a first upper surface, and an access bore configured to receive an expansion tool;
an upper support movably coupled to the lower support and comprising a second upper surface, a second lower surface, and a control aperture, wherein the control aperture is defined by the upper support and extends though the second upper surface; wherein the expandable implant is configured to expand between a first, collapsed position and a second, expanded position such that movement of the upper support relative to the lower support changes an angle defined between the first lower surface and the second upper surface as the expandable implant expands;
a control shaft rotatably coupled to the lower support, wherein the control shaft includes a head configured to receive the expansion tool, wherein manipulation of the expansion tool causes the upper support to move relative to the lower support; and
a control member coupled to the control shaft, the control member comprising:
a base member threadingly coupled to the control shaft and rotatably fixed relative to the lower support;
a first pivot member coupled to a first side of the base member, wherein a first ramp surface of the pivot member is configured to engage a second ramp surface defining the control aperture such that the pivot member is slidingly received in the control aperture;
a second pivot member coupled to a second side of the base member opposite the first side and slidingly received in the control aperture.

16. The expandable implant of claim 15, wherein the control shaft is translationally fixed relative to the lower support.

17. The expandable implant of claim 15, wherein the expandable implant defines a cavity providing access to an interior of the expandable implant.

18. The expandable implant of claim 15, wherein the base member includes a flat bottom surface that slidingly engages a surface of the lower support.

19. An expandable implant comprising:
a lower support comprising a first lower surface, a first upper surface, and an access bore configured to receive an expansion tool;
an upper support movably coupled to the lower support and comprising a second upper surface, a second lower surface, and a control aperture, wherein the control aperture is defined by the upper support and extends though the second upper surface; wherein the expandable implant is configured to expand between a first, collapsed position and a second, expanded position such that movement of the upper support relative to the lower support changes an angle defined between the first lower surface and the second upper surface as the expandable implant expands;
a control shaft rotatably coupled to the lower support, wherein the control shaft includes a head configured to receive the expansion tool, wherein manipulation of the expansion tool causes the upper support to move relative to the lower support; and
a control member coupled to the control shaft, the control member comprising:
a base member threadingly coupled to the control shaft and rotatably fixed relative to the lower support;
a first pivot member coupled to a first side of the base member and sliding received in the control aperture; and
a second pivot member coupled to a second side of the base member opposite the first side and sliding received in the control aperture;

a first pivot pin extending through a first side of the upper support and into the lower support; and a second pivot pin extending through a second side of the upper support opposite the first side of the upper support and into the lower support.

\* \* \* \* \*